US007856321B2

(12) United States Patent
Lanza et al.

(10) Patent No.: US 7,856,321 B2
(45) Date of Patent: Dec. 21, 2010

(54) MODELING BIOLOGICAL EFFECTS OF MOLECULES USING MOLECULAR PROPERTY MODELS

(75) Inventors: Guido Lanza, San Francisco, CA (US); Nigel P. Duffy, San Francisco, CA (US); Paul Boardman, South San Francisco, CA (US)

(73) Assignee: Numerate, Inc., San Bruno, CA (US)

( * ) Notice: Subject to any disclaimer, the term of this patent is extended or adjusted under 35 U.S.C. 154(b) by 0 days.

(21) Appl. No.: 11/304,209

(22) Filed: Dec. 14, 2005

(65) Prior Publication Data

US 2006/0161407 A1 Jul. 20, 2006

Related U.S. Application Data

(60) Provisional application No. 60/636,645, filed on Dec. 16, 2004.

(51) Int. Cl.
*G01N 33/48* (2006.01)
*G06G 7/48* (2006.01)

(52) U.S. Cl. .......................................... 702/19; 703/11

(58) Field of Classification Search ....................... None
See application file for complete search history.

(56) References Cited

U.S. PATENT DOCUMENTS

| | | | | |
|---|---|---|---|---|
| 2003/0074141 | A1 * | 4/2003 | Russell | 702/19 |
| 2004/0180322 | A1 | 9/2004 | Grass et al. | |
| 2004/0249664 | A1 | 12/2004 | Broverman et al. | |
| 2005/0119832 | A1 | 6/2005 | Schmitt et al. | |
| 2005/0209785 | A1 | 9/2005 | Wells et al. | |
| 2005/0260663 | A1 | 11/2005 | Solomon | |

OTHER PUBLICATIONS

Supplementary European Search Report mailed Jan. 19, 2009 for European Application No. EP 05849722.3.

Guiseppina, Gini et al., "Combining Unsupervised and Supervised Artificial Neural Networks to Predict Aquatic Toxicity," Journal of Chemical Information and Computer Sciences, vol. 44, No. 6, Nov. 2004, pp. 1897-1902, XP-002508900, ISSN: 0095-2338.

Lilly, Patrick D. et al., "A Physiologically Based Pharmacokinetic Description of the Oral Uptake, Tissue Dosimetry, and Rates of Metabolism of Bromodichloromethane in the Male Rat," Toxicology and Applied Pharmacology, vol. 150, No. 2, Jun. 1998, pp. 205-217, XP-002508901, ISSN: 0041-008X.

Conolly, Rory B. et al., "Biologically Based Pharmacodynamic Models: Tools for Toxicological Research and Risk Assessment," Annual Review of Pharmacology and Toxicology 1991, vol. 31, 1991, pp. 503-523, XP-002508902, ISSN: 0362-1642.

Yan, Shengquan et al., "A Dynamic Meta-Model Approach to Genetic Algorithm Solution of a Risk-Based Groundwater Remediation Design Model," Proceedings of the World Water and Environmental Resources Congress, held in Salt Lake City, Utah, Jun. 27-Jul. 1, 2004, pp. 1-10, XP008099911.

International Search Report and Written Opinion mailed Mar. 9, 2007 for PCT Application No. PCT/US05/45344.

International Preliminary Report on Patentability mailed Jun. 28, 2007 for PCT Application No. PCT/US2005/045344.

Hilario, Melanie et al., "Fusion of Meta-knowledge and Meta-data for Case-Based Model Selection," PKDD 2001, LNAI 2168, © Springer-Verlag Berlin Heidelberg 2001, pp. 180-191.

Germani, Massimiliano et al, "In vitro cell growth pharmacodynamic studies: a new nonparametric approach to determining the relative importance of drug concentration and treatment time," Cancer Chemotherapy and Pharmacology, 2003, vol. 52, pp. 507-513.

Urquidi-MacDonald, Mirna et al., "Abciximab pharmacodynamic model with neural networks used to integrate sources of patient variability," Clinical Pharmacology and Therapeutics, 2004, vol. 75, pp. 60-69.

* cited by examiner

*Primary Examiner*—Eric S Dejong
(74) *Attorney, Agent, or Firm*—Moser IP Law Group

(57) ABSTRACT

Method, apparatus, and article of manufacture for modeling the biological effects of a molecule are disclosed. A machine learning application may be configured to process a set of training examples regarding a biological property of interest. Once trained, the machine learning application may be configured to generate a prediction regarding a property of interest for a test molecule. Embodiments of the invention provide a meta-model configured to generate a biological effect prediction for a molecule based on the predictions generated for the test molecule by a plurality of molecular property models.

16 Claims, 5 Drawing Sheets

MODELING BIOLOGICAL EFFECTS OF MOLECULES USING MOLECULAR PROPERTY MODELS

CROSS-REFERENCE TO RELATED APPLICATIONS

This application claims the benefit of U.S. provisional application, Ser. No. 60/636,645 filed on Dec. 16, 2004, which is incorporated herein by reference in its entirety. Also, this application is related to the following commonly assigned U.S. patent applications: "Methods For Molecular Property Modeling Using Virtual Data" (Ser. No. 11/074,587 filed on Mar. 8, 2005), "Estimating the Accuracy of Molecular Property Models and Predictions" (Ser. No. 11/172,216 filed on Jun. 29, 2005), and "Molecular Property Modeling using Ranking" (Ser. No. 11/172,215 filed on Jun. 29, 2005), each of which is incorporated herein by reference in its entirety.

BACKGROUND OF THE INVENTION

1. Field of the Invention

Embodiments of the present invention are generally related to machine learning. More specifically, embodiments of the present invention are related to machine learning techniques used to predict the biological effects of a molecule.

2. Description of the Related Art

Molecules are continually being introduced into the marketplace or environment, (e.g., industrial detergents, industrial discharge, pharmaceuticals and cosmetics). Sometimes, such molecules may have unknown or undesirable biological effects (e.g. they may have some level of toxicity on humans, flora or fauna). It is of great benefit for organizations introducing such molecules, and for society in general, to anticipate such effects as early as possible. In this way it may be possible to take remedial action (e.g., not introducing the molecule, re-designing the molecule to remove the effect, or limiting the introduction of the molecule). Also, it is possible to identify molecules that have desirable biological effects, and the pharmaceutical industry spends billons of dollars each year to test and identify potentially useful molecules.

The high-level effects of a molecule, both desirable (e.g. anti-inflammatory) and undesirable (e.g., toxicity), are overwhelmingly related to some lower level bio-chemical pathway. More specifically, high-level effects often result from the interaction of a molecule with a binding site on a protein present in some bio-chemical pathway. And a high-level effect of a molecule may result from the interaction of the molecule with multiple proteins in multiple pathways. In many cases, the particular protein(s) and pathway(s) may not be fully known or understood, even though the correlation between a high-level effect and the molecule may be well documented. For example, gabapentin NEURONTIN from Parke-Davis/Pfizer is used to treat epilepsy and neuropathic pain; however, the protein targets underlying the actions of these compounds are unknown.

Currently, two general approaches are used for identifying the high level effects of a molecule. The first is to perform laboratory experiments using the molecule. The effects of the molecule may also be analyzed in various clinical trials, including trials with human subjects. For example, the pharmaceutical testing required by the United States Food and Drug Administration requires a variety of clinical studies be performed before a molecule may be distributed for medical purposes. However, one drawback to this approach is that physical laboratory experiments and clinical trials are typically both costly and time consuming, making them prohibitive to perform for more than limited number of candidate molecules. Accordingly, this approach is often used only after identifying a candidate molecule as being potentially beneficial.

A second approach is to perform in silico simulations configured to generate predictions about the properties of a molecule. The term "in silico" is used to reference simulations performed using computer software applications that model the real-world behavior of the molecule. The simulation may be based on the physical characteristics of the molecule (e.g., structure, molecular weight, electron density, etc) and the characteristics of the simulated environment (e.g., the shape, position and characteristics of a particular protein receptor). Thus, an in silico simulation may be used to simulate the interaction between a molecule and a single protein target. The output of the simulation may include a prediction regarding a biological effect or property of the molecule, e.g., the binding affinity of the molecule against the protein target. Models have been developed that can predict these kinds of low-level properties with a reasonable degree of accuracy. However, the accuracy of in silico simulations used to predict high-level effects have typically been very poor. Thus, even though some protein/molecule interaction may be known to be related to an observed high-level effect, no one has currently been able to bridge the gap between using an in silico simulation to predict a low-level activity regarding a molecule and using an in silico simulation to predict whether a molecule is likely to have a given a high-level effect when introduced into a biological system (e.g., a human individual).

The state of the art in in silico prediction for low-level effects is to construct models based on a topological representation of a molecule, or based on simple three-dimensional models of a molecule. For example, current in silico simulations typically rely on data that may include the position, orientation, or electrostatic properties of the molecule in 3D space. This approach, however, has typically resulted in inaccurate predictions regarding high-level biological effects. A number of reasons may account for this. For example, the representation of the molecule is too high dimensional for the high level effect being modeled, too few data points may be used to model a high-level effect, the representation fails to capture the relevant information, e.g., the "cause" of the biological effect is not a property (or function) of the orientation or electrostatic properties of the molecule, these and other shortcomings may all contribute to the poor results obtained from current in silico simulations.

Accordingly, there remains a need for improved techniques for predicting the biological effects of molecules in general, and for modeling biological effects that may result from the interaction between a test molecule and a biological system.

SUMMARY OF THE INVENTION

The present invention generally provides methods, systems, and articles of manufacture for modeling the biological effects of molecules. Embodiments of the invention predict the biological effect of a molecule of interest using a molecular properties model configured using machine learning techniques.

One embodiment of the invention provides a method for using a machine-learned meta-model to generate a prediction regarding a biological effect of a test molecule. The method generally includes training a plurality of molecular property models using a first set of training data, wherein each trained molecular property model is configured to generate a predictiontion regarding a property of interest of a test molecule modeled by each respective molecular properties model. In one embodiment of the invention, the molecular property model is a single target activity model. The method generally further includes training the meta-model using the set of training data, wherein the trained meta-model is configured to generate the prediction regarding the biological effect of the test molecule from the predictions generated for the test molecule by each of the plurality of trained molecular property models.

Once trained, the meta-model may be used to generate a prediction for a test molecule. Generally, such a prediction is obtained by selecting the test molecule, generating a representation of the test molecule appropriate for the plurality of molecular property models and providing the representation of the test molecule to the molecular property models to obtain the prediction regarding the test molecule from each of the of the molecular property models. The predictions are then supplied to the meta-model, which generates a prediction for the test molecule regarding the biological effect.

Each of the molecular property models and the meta-model may be "trained" by performing a selected machine learning algorithm, although not necessarily the same algorithm need be performed by each model. Representative machine learning algorithms include a classification learning algorithm, a kernel based learning algorithm, a Boosting algorithm, RankBoost algorithm, Alternating Decision Trees algorithm, Support Vector Machines algorithm, a Perceptron algorithm, Winnow, a Hedge Algorithm, decision trees, neural networks, genetic algorithms, or genetic programming algorithm.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. The appended drawings, however, illustrate only typical embodiments of this invention and are, therefore, not to be considered limiting of its scope, for the invention may admit to other equally effective embodiments.

DETAILED DESCRIPTION

Figure 1:
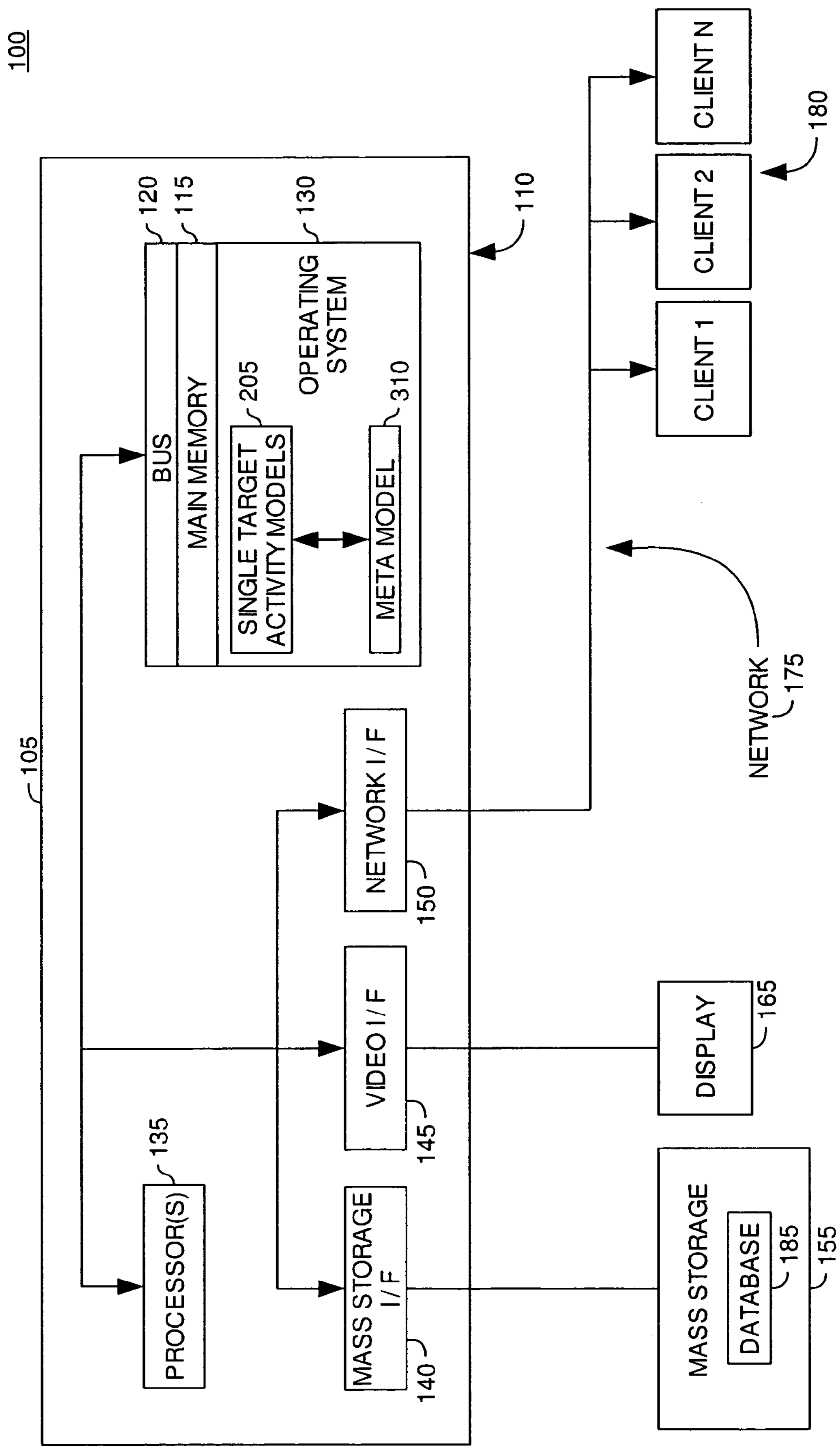
FIG. 1 illustrates a computing environment that may be used to implement an embodiment of the invention.

Generally, machine learning techniques may be used to develop a software application—referred to as a model—that improves its ability to perform a task as it analyzes more data related to the task. Often, the task is to predict an unknown attribute or quantity from known information (e.g., the binding affinity of a molecule against a specific protein target). Typically, a machine learning model is trained using a set of training examples. Each training example may include an example of an object, along with a value for the otherwise unknown property of the object (e.g., a representation of a molecule and a known binding affinity for the molecule and a protein). By processing a set of training examples that includes both an object and a property value for the object, the model "learns" what attributes or characteristics of the object are associated with a particular property value. This "learning" may then be used to predict the property or to predict a classification for other objects.

In the fields of bioinformatics and computational chemistry, machine learning applications may be used to develop models of various molecular properties. Oftentimes, such models may be developed to predict whether a particular molecule will exhibit a property of interest being modeled. For example, models may be developed to model biological properties such as pharmacokinetic or pharmacodynamic properties, physiological or pharmacological activity, toxicity or selectivity. Other examples of properties of interest that may be modeled include models that predict chemical properties such as reactivity, binding affinity, or properties of specific atoms or bonds in a molecule, e.g. bond stability. Similarly, models may be developed that predict physical properties such as the melting point or solubility of a substance. Further, molecular models may be developed that predict properties useful in physics-based simulations such as force-field parameters or the free energy states of different possible conformations of a molecule.

The training examples used to train a molecular properties model may include a description for a molecule (e.g., the atoms and bond structure of a particular molecule) and data regarding a property of interest for the molecule. Collectively, the training examples are referred to as a "training set" or as "training data." Data regarding the property of interest may include (i) a value from a continuous range (e.g., the solubility of a molecule at a solute temperature or the known binding affinity between the molecule in the example and the protein target being modeled), or (ii) a label asserting presence or absence of the property of interest relative to the molecule included in the training example. Another form of a training example includes a ranking of two or more molecules. A ranking is used to order to or more molecules relative to the property being modeled. Detailed examples of ranking techniques used in a machine learned molecular property model are described in commonly assigned U.S. patent application Ser. No. 11/172,215, filed Jun. 29, 2005 and titled "Molecular Property Modeling Using Ranking."

The molecules included in the training data may be selected from molecules with a known value for the property being modeled. The known value may be based on experimentation, simulation, analysis, or even reasonable assumptions regarding the property being modeled. In one embodiment, assumed values may be used for one or more of the molecules represented in the training data. Detailed examples of using assumed values for some activity measurements are described in a commonly owned co-pending U.S. patent application, Ser. No. 11/074,587 titled "Methods for Molecular Property Modeling Using Virtual Data."

The training set is then used to train a molecular properties model. In one embodiment, the model performs a selected machine learning algorithm using the training set. Once trained, the model may be used to generate a prediction about a test molecule, relative to the property of interest. For example, the model may be configured to predict the binding affinity of a test molecule with a protein target represented by the model. In this example, the binding affinity is the property of interest. When a representation of the test molecule is supplied to the trained model, the output may comprise a prediction regarding the value of the property being modeled for the test molecule. The predictions may take the form of a value from a continuous range of values, a discrete value, or a ranking of two or more molecules, relative to the property of interest.

Embodiments of the invention harness the predictions generated by a plurality of these models (referred to herein as "single target activity models") by using the output of these models as input for a meta-model. The single target activity models are a type of molecular properties model. As used herein, a single target activity model refers to a molecular properties model configured to predict properties such as the activation or inhibition properties of a molecule against a protein, whether a molecule will bind to any (or to a specific) receptor on a protein, or combinations of these properties. Other forms of molecular property models may be used to generate predictions that are used by the meta-model.

Oftentimes, a biological effect may have many different underlying causes. For example, a risk of heart attack may be affected by interfering with the HERG $K^+$ protein, increasing blood pressure, or by increasing the risk of blood clots. At the molecular level, these biological effects are overwhelmingly caused by the interaction of a molecule with a protein target, or targets, present in a biochemical pathway. A meta-model configured according to an embodiment of the invention, however, may be able to predict whether a molecule will have the biological effect, without having to identify the particular protein(s) involved in the interaction, or the mechanism of action underlying the biological effect.

The more single target activity models used to generate input data for the meta-model, the more the single target activity models may become representative of the complete set of proteins in a given biological system. That is, even though a protein that is responsible for a given biological effect of a molecule may not be modeled by one of the single target activity models, the meta-model may still accurately predict that the molecule possesses the biological effect. Thus, the models that are included may act as a surrogate for proteins that are not represented by a single target activity model. Accordingly, broad biological effects, such as toxicity, or increased potential for both desirable and undesirable effects may be modeled, even though models of the actual protein targets responsible for the high-level effect may not even exist. For example, the anti-tuberculosis effects of a molecule may be modeled without using any models of tuberculosis proteins.

In one embodiment, the meta-model is configured to generate a prediction regarding the biological effect of a molecule. For example, a prediction may specify whether a particular test molecule has, does not have, causes, or does not cause, the biological effect property being modeled. Any relevant biological effect may be modeled. For example, among others, the meta-model may be configured to predict undesirable effects such as increasing risk of heart attack, toxicity, or carcinogenic properties of a molecule, or may be configured to predict desirable properties such as the analgesic, anti-inflammatory, anti-cancer, antibacterial or antiviral properties of the molecule.

Once both the plurality of single target activity models and the meta-model have been trained, the output predictions generated by the plurality of single target activity models are used to generate an input to the meta-model. In one embodiment, the input data includes a representation of the test molecule appropriate for the meta-model and the predictions of each of the single target activity models. Thus, embodiments of the invention provide a hierarchy of models wherein the meta-model is trained using the outputs of the plurality of single target activity models. Although described herein using a two-level hierarchy, the techniques of the present invention may be extended to create deeper hierarchies of models. For example, the output of a plurality of meta-models may be used as input for a second-order meta-model.

Embodiments of the invention may be implemented using any available computer system and adaptations are contemplated for both known and later developed computing platforms and hardware. Accordingly, the methods described below may be carried out by software applications configured to execute on computer systems ranging from single-user workstations, client server networks, large distributed systems employing peer-to-peer techniques, or clustered grid systems. In one embodiment, a high-speed computing cluster such as a Beowulf cluster or other clustered configuration may be used. Those skilled in the art will recognize that a clustering is a method for creating a high-performance computing environment by connecting inexpensive personal computer systems over high-speed network paths.

Further, the computer systems used to practice the methods of the present invention may be geographically dispersed across local or national boundaries using a data communications network such as the Internet. Moreover, predictions generated for a test molecule at one location may be transported to other locations using well known data storage and transmission techniques, and predictions may be verified experimentally at the other locations. For example, a computer system may be located in one country and configured to generate predictions about the property of interest for a selected group of molecules, this data may then be transported (or transmitted) to another location, or even another country, where it may be the subject of further investigation e.g., laboratory confirmation of the prediction or further computer-based simulations.

An Exemplary Computing Environment

Embodiments of the invention may be implemented as computer software products (programs) for use with computer systems like the one illustrated in FIG. 1. Such programs may be contained on a variety of signal-bearing media. Examples of signal-bearing media include (i) information permanently stored on non-writable storage media (e.g., a CD or DVD disk); (ii) alterable information stored on writable storage media (e.g., floppy disks within a diskette drive or hard-disk drive); and (iii) information conveyed to a computer by a communications network, including wireless communications. The latter embodiment specifically includes information made available on the Internet and other networks. Such signal-bearing media, when carrying computer-readable instructions that implement the methods of the invention, represent embodiments of the invention.

Referring now to FIG. 1, a computing environment 100 is shown. In general, the environment 100 includes a first computer system 105 and a plurality of client computer systems each connected via network 175. The computer system 105 may represent any type of computer, computer system or other programmable electronic device, including a client computer, a server computer, a portable computer, an embedded controller, a PC-based server, a minicomputer, a midrange computer, a mainframe computer, a grid based, or clustered computer system and other computers adapted to support embodiments of the invention.

Illustratively, the computer system 105 comprises a networked system. However, the computer system 105 may also comprise a standalone device. In any case, it is understood that FIG. 1 is illustrates one possible configuration for a computer system 105.

The embodiments of the present invention may also be practiced in distributed computing environments in which tasks are performed by remote processing devices that are linked through communications network 175. The computer system 105 may include a number of operators and peripheral systems as shown, for example, by a mass storage interface 140 connected to a direct access storage device 155 containing a database 185, by a video interface 145 operable connected to a display 165, and by a network interface to network 175 (e.g. WAN, LAN). The display 165 may be any video output device for outputting viewable information.

Computer system 105 is shown comprising at least one processor 135, which obtains instructions and data via a bus 120 from a main memory 115. The processor 135 could be any processor adapted to support the methods of the invention.

The main memory 115 is any memory sufficiently large to hold the necessary programs and data structures. Main memory 115 could be one or a combination of memory devices, including Random Access Memory, nonvolatile or backup memory, (e.g., programmable or Flash memories, read-only memories, etc.). In addition, memory 115 may be considered to include memory physically located elsewhere in a computer system 105, for example, any storage capacity used as virtual memory or stored on a mass storage device (e.g., direct access storage device 155) or on another computer coupled to the computer system 105 via bus 120 or network 175.

The memory 115 is shown configured with an operating system 130. The operating system 130 is the software used for managing the operation of the computer system 110. As shown, the memory includes a plurality of single target activity models 205 in communication with a meta-model 310, both of which are described in greater detail below.

Figure 2:
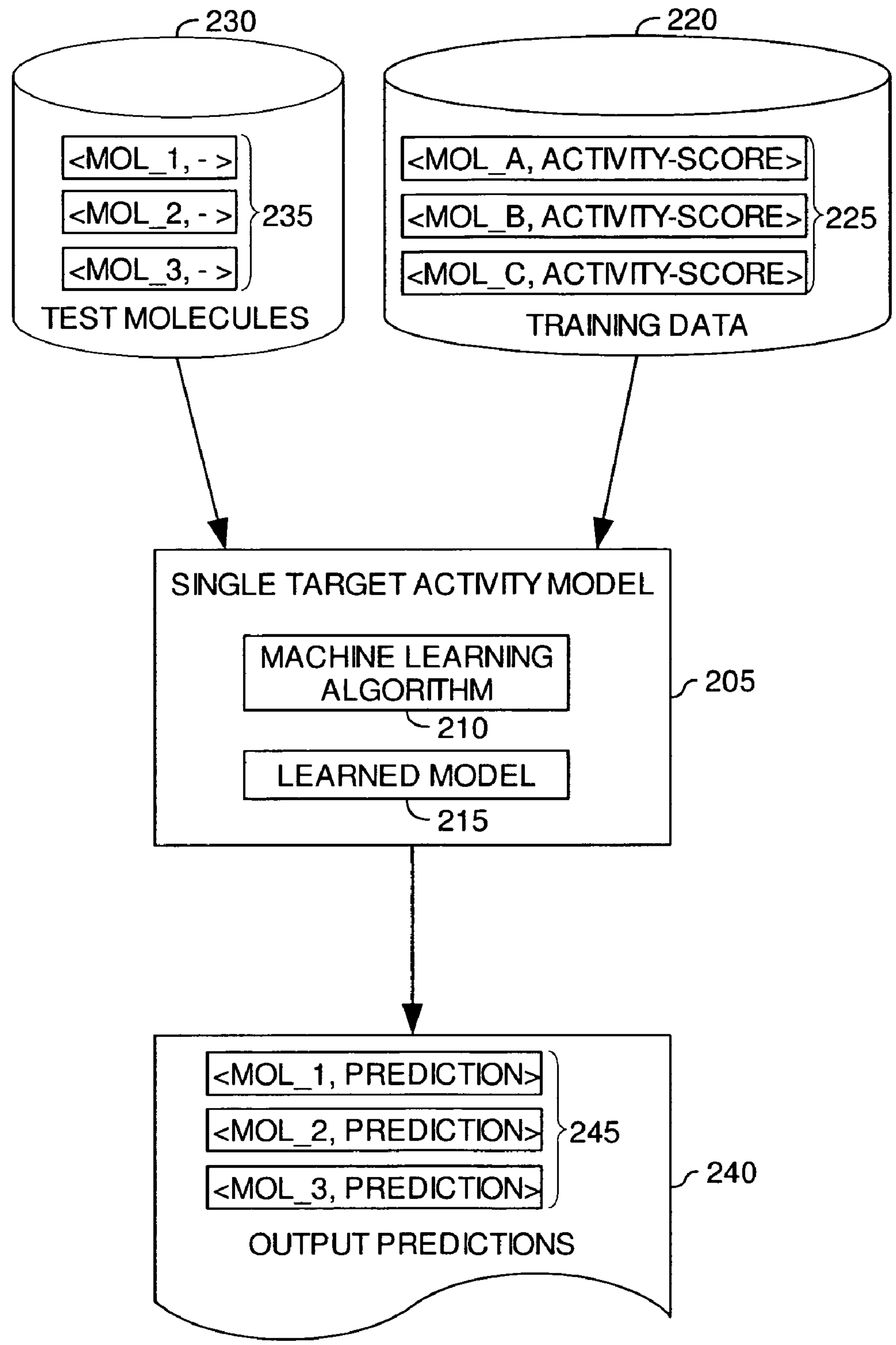
FIG. 2 is a block diagram illustrating a molecular properties model, according to one embodiment of the invention.

FIG. 2 is a block diagram 200 illustrating a single target activity model 205, according to one embodiment of the invention. As shown, FIG. 2 includes a single target activity model 205, a set of test molecules 230, a set of training data 220, and output predictions 240. In one embodiment, the single target activity model 205 may be configured to perform a machine learning algorithm 210 using training data 220 to generate the learned model 215. Once generated, the learned model 215 may be used to generate output predictions 240 for test molecules 230.

The machine learning algorithm 210 performed by the model 205 may include both currently known and later developed machine learning algorithms. For example, the learning algorithm 210 may include at least one of Boosting, a variant of Boosting, Alternating Decision Trees, Support Vector Machines, the Perceptron algorithm, Winnow, the Hedge Algorithm, an algorithm constructing a linear combination of features or data points, Decision Trees, Neural Networks, Genetic Algorithms, Genetic Programming, logistic regression, Bayes nets, log linear models, Perceptron-like algorithms, Gaussian processes, Bayesian techniques, probabilistic modeling techniques, regression trees, ranking algorithms, Kernel Methods, Margin based algorithms, or linear, quadratic, convex, conic or semi-definite programming techniques or any modifications of the foregoing.

The training data 220 may be selected according to any of the techniques described above at paragraphs 20-28. However selected, training data 220 is used by the machine learning algorithm 210 to train the single target activity model 205 and generate learned model 215. Illustratively, each training example 225 provides a vector that includes a representation of the molecule appropriate for the machine learning algorithm 210 and a value (labeled as "Activity_Score") for the property being modeled by single target activity model 205. Illustratively, training data 220 includes three vectors, each representing a training example 225. Specifically. <mol_A, Activity_score>, <mol_B, Activity_score>, and <mol_C, Activity_score> to illustrate three training examples represented as a vector. As shown, each training example 225 includes a molecule representation element and an activity score regarding the property being modeled by model 205. In practice however, it is contemplated that significantly more examples would be included in the training data 220.

Once the single target activity model 205 performs the machine learning algorithm 210 to generate the learned model 215, it may be used to generate predictions for test molecules 230. Illustratively, test molecules 230 includes thee test candidates 235. Like the training examples 225, each test candidate 235 may include representation of a molecule stored in a vector. However, instead of including an activity score for the molecules represented by "mol__1," "mol__2," and "mol__3," the second element of the vector representation is not included for the test candidates 235; instead this is the information predicted for each test candidate 235 using learned model 215. Accordingly, output predictions 240 include the three test candidates 245 (namely, "mol__1", "mol__2", and "mol__3"), with a completed vector representation that includes a prediction for the property modeled by single target activity model 205.

Figure 3:
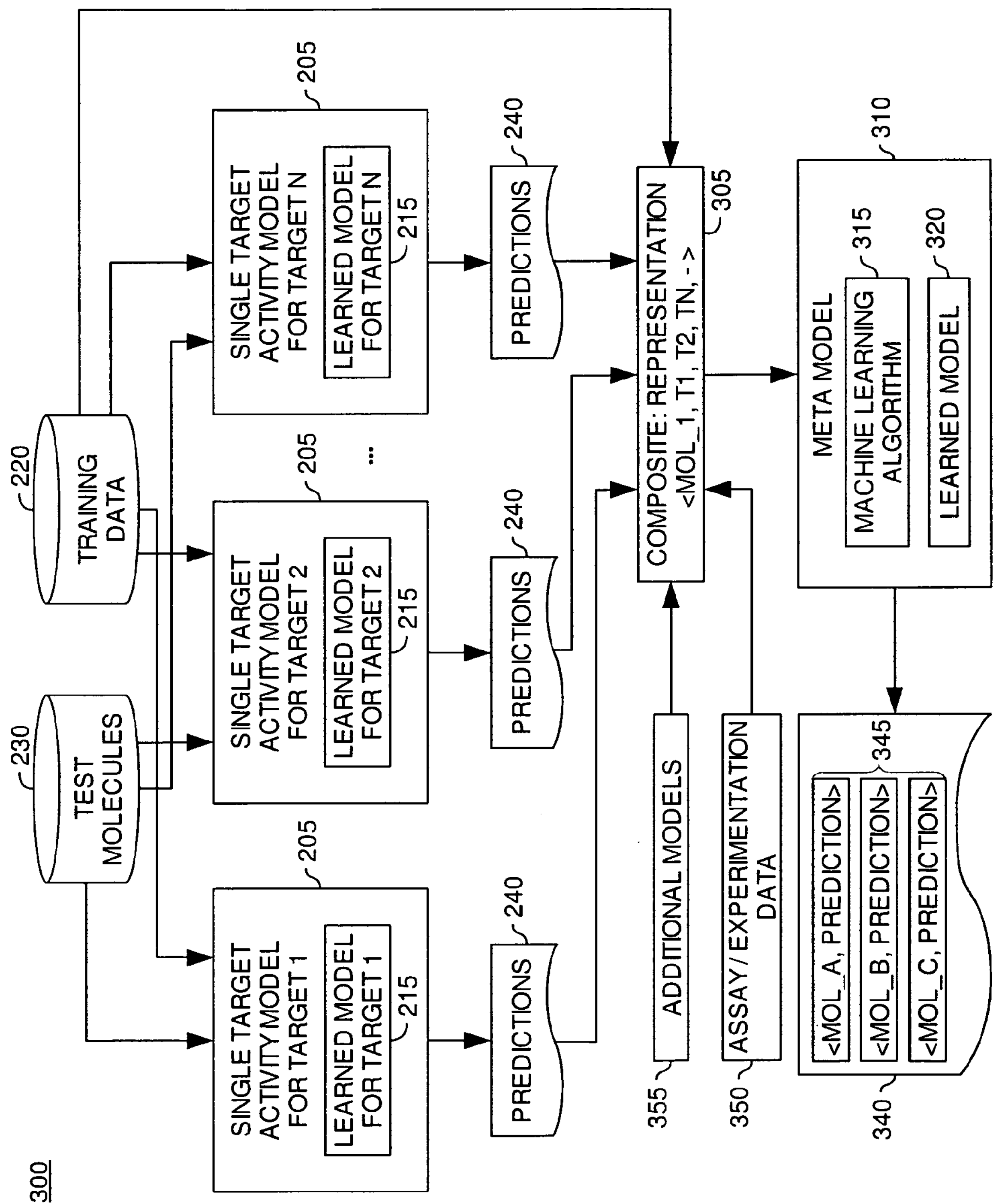
FIG. 3 illustrates a meta-model configured to learn from a hierarchy of single-target activity models, according to one embodiment of the invention.

FIG. 3 is a block diagram 300 illustrating a meta-model 310 configured to learn from a hierarchy of single-target activity models 205, according to one embodiment of the invention. As shown, diagram 300 includes three single target activity models 205. In practice however, it is contemplated that significantly more single target activity models 205 would be used to create meta-model 310. Like the view of a single target activity model 205 illustrated in FIG. 2, each of the three models 205 may be configured to process a set of training data 220 to train a learned model 215. For example, each single target activity model 205 may represent a different protein (or receptor on a protein), and the learned models 215 may be configured to predict the binding affinity between a test molecule and the particular protein represented by each respective model 205. The predictions generated by a single target activity model 205 may be stored in a data set of predictions 240.

Also like single target activity model 205, meta-model 310 may be configured to perform a machine learning algorithm 315 using training data 220. The machine learning algorithm 315 may be selected from any one of the (or other) machine learning algorithms identified above in paragraph 39. In one embodiment, the training examples 225 used to train the meta-model 310 may comprise a composite of the training examples 225 used to train each of the single target activity models 205. For example, using the first training example 225 illustrated in FIG. 2, a composite representation 305 may be styled as vector similar to the following:

<mol_A, Score__1, Score__2, Score_N, value_for_modeled_effect>

In this vector "mol_A" provides a representation of the molecule appropriate for machine learning algorithm 315. The Score__1, Score__2, and Score_N components represent the value supplied to a machine learning algorithm 210 performed by each different single target activity model 205. Finally, the "value_for_modeled_effect" component may identify a value for the biological effect being modeled by meta-model 310.

Optionally, the composite representation 305 may include additional information obtained from additional models 355 or from biological assays or other experimental data 350. For example, in an alternative embodiment, training data 220 may include the output data generated from physical laboratory experiments. In such an embodiment, a meta-model 310 may be trained using the outputs from a plurality of biological assays or other laboratory experimentation performed using a particular molecule and a suite of different protein targets. Following this approach, each molecule in the training data is screened by performing a physical experiment and the results of these experiments are used to generate the composite representation 305 for the learning algorithm 310. Additional models 355 may be used to provide additional information to include in composite representation 305. Other embodiments extend the methods illustrated in FIG. 3 by including other models or measurements into the composite representation 305. For example, in addition to predictions or measurements of activity against a protein target generated by the single target activity models 205, properties such as predictions or measurements of solubility, blood brain barrier permeability, or other physical, chemical or biological properties of a molecule may be predicted using the techniques disclosed herein.

Note however, that a composite representation 305 used as a training example or a test candidate need not be "complete." That is, for a given composite representation 305, there may be a predicted value for less than all of the single target activity models included in the meta-model hierarchy.

Once the machine learning algorithm 310 is used to generate learned model 320 from the training data 220, the meta-model 310 may be used to generate predictions regarding the biological effect of a test molecule 230. Illustratively, predictions 340 include a prediction generated for three candidate molecules 345 regarding the biological effect modeled by meta-model 310.

In one embodiment, a prediction for a test molecule 230 is generated by supplying a representation of the test molecule 230 to each respective single target activity model 205. The form of the representation may be configured to be appropriate for the particular learned model 215. Using the outputs of these models 205 (i.e., using predictions 240) a composite representation 305 may then be generated for the test molecule. The composite representation may include a representation of the test molecule in a form appropriate for the learned model 320, the prediction regarding the property of interest and the test molecule output by each single target activity model 205, and any additional information provided by additional models 355 or experimental data 350. Thereafter, the learned model 320 may be configured to output a prediction 345 for test molecule 230 identified by composite representation 305. Depending on the configuration of learned model 320, the meta-model 310 may be configured to predict a particular test molecule 230 has, does not have, causes, or does not cause, the biological effect property being modeled. Predictions 345 illustrate a generic "prediction" result generated by the meta-model 310. Alternatively (or additionally) meta-model may be configured to predict a value for a biological effect selected from a range of continuous values, or from a set of discrete choices. In another alternative the meta-model may be configured to predict a ranking of two or more test molecules relative to the biological effect modeled by the meta-model.

Figure 4:
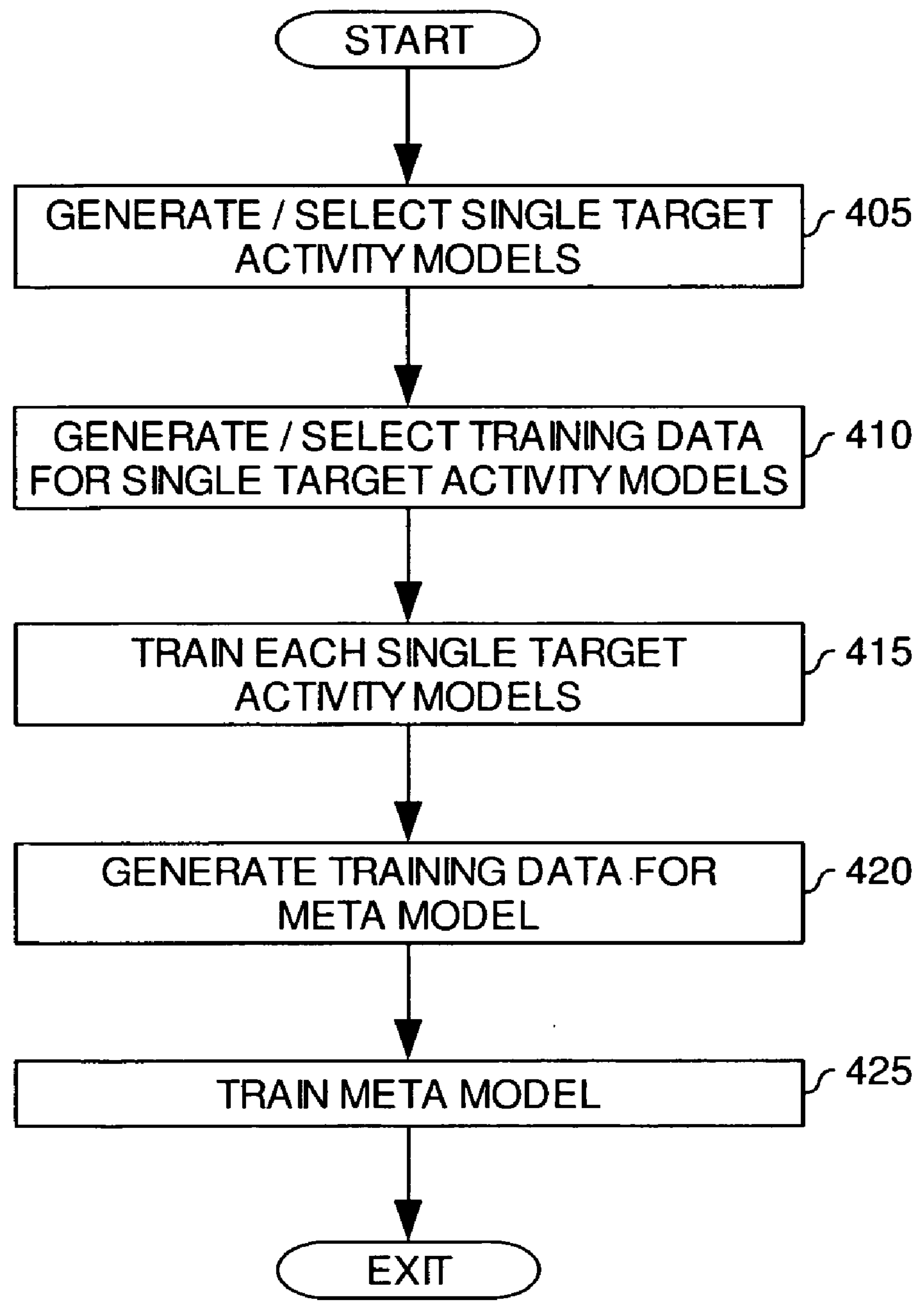
FIG. 4 illustrates a method for training a meta-model using the output from a plurality of single target activity models, according to one embodiment of the invention.

FIG. 4 illustrates a method for constructing a meta-model 310 configured to predict a biological effect of a molecule based on the predictions of a plurality of single target activity models 205, according to one embodiment of the invention. The method 400 begins at step 405 where the set of single target activity models 205 is selected. In one embodiment, the single target activity models 205 may be selected based on the available training data, the measured (or predicted) accuracy of the models, and on any other relevant criteria in a particular case. Generally, however, the more single target activity models 205 that are available, the more accurate the predictions generated by meta-model 310 regarding the high-level biological effect may become.

At step 410, a set of training data is selected to train the single target activity models 205. Although complete one-to-one correspondence is not required, a molecule selected to be included in the training data 220 is typically used to generate a training example 225 for each single target activity model 205. In one embodiment, the training examples 225 are represented as a vector that includes the representation of the molecule and a value for the property being modeled. At step 415, the training examples generated at step 410 are used to train the single target activity models 205. At this step, each single target activity model 205 performs the selected machine learning algorithm 210 to generate learned model 215.

At step 420, the training examples generating training data for the meta-model 310. In one embodiment, each training example for the meta-model 310 may include a representation of a molecule represented by the example, the prediction for the molecule from each of the single target activity models, along with a value for the property of interest. At step 450, the training examples are used by meta-model 310 to perform machine learning algorithm 315 and generate learned model 320. Thus the training data may also be used to train the meta-model 310. In one embodiment, the training examples used to train the meta-model 310 may include a representation of the molecule and a value for the property of interest for each of the single target activity models 205 and a value for the biological effect being modeled by meta-model 310.

Figure 5:
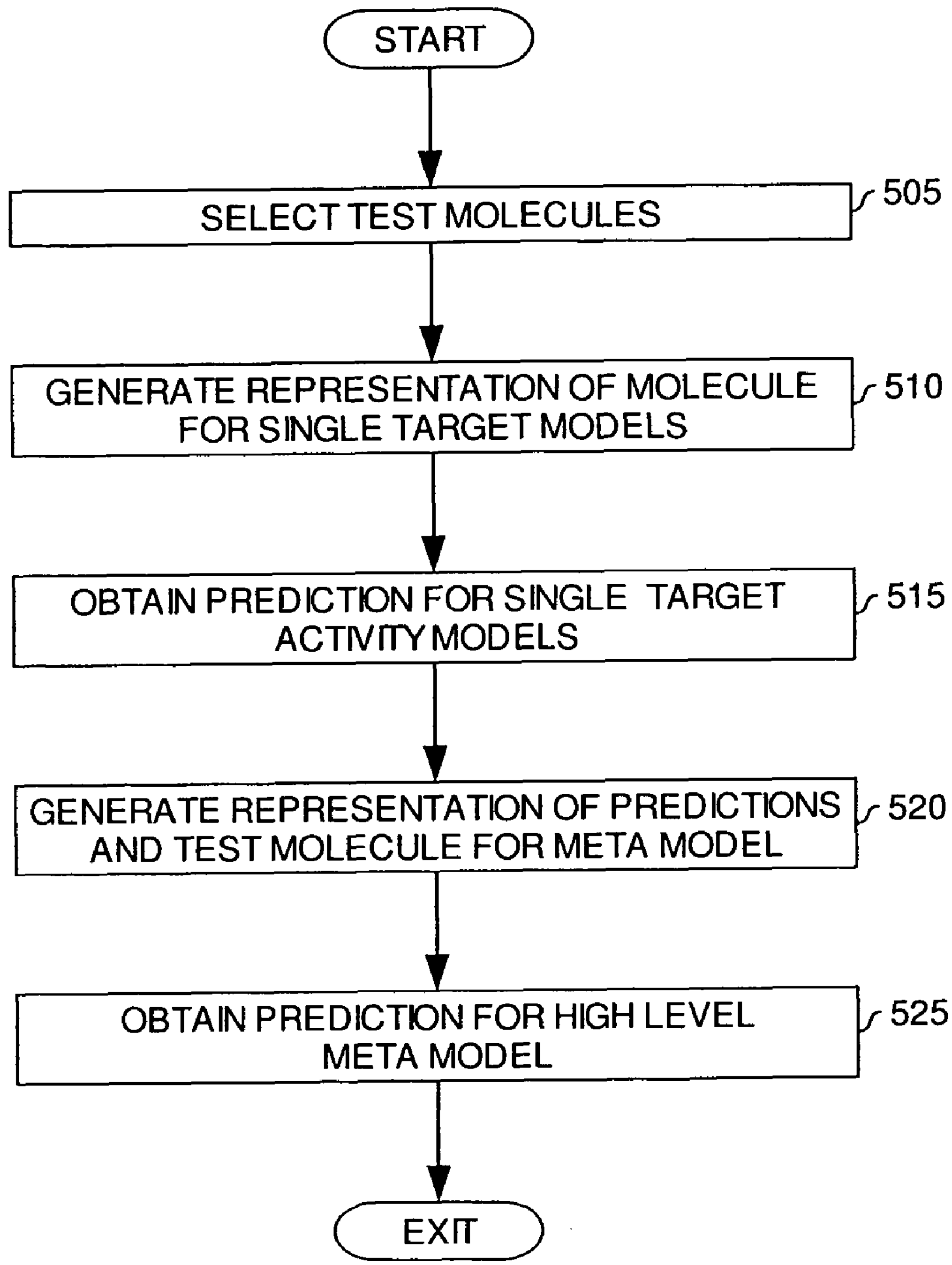
FIG. 5 illustrates a method for generating a prediction related to a biological effect of a molecule using a meta-model trained according to the method illustrated in FIG. 4, according to one embodiment of the invention.

FIG. 5 illustrates a method 500 for generating a prediction related to a high level biological effect of a molecule using the learned model 320 of meta-model 310 generated using the method illustrated in FIG. 4, according to one embodiment of the invention.

The method 500 begins at step 505 where a set of test molecules 230 is selected. At step 510, a representation of the test molecules 230 is generated in a form appropriate for the learned model 215 used by each respective single target activity model 205. At step 515, the representations of the test molecule is supplied to each of the learned models 215, which, in response, may be configured to generate a prediction regarding the test molecule and the property modeled by each of the single target activity models 205. For example, in an embodiment where the single target activity models predict the binding affinity between the test molecule and the protein represented by a single target activity model 205, the prediction may comprise a value for binding affinity.

At step 520, the set of predictions generated at step 515 are included in a composite representation 305 that includes both the predictions output at step 515 and a representation of test molecule 230 in a form appropriate for the learned model 320 of meta-model 310. At step 525, the representation of the test molecule 230 is supplied to learned model 320, which, in response, may be configured to generate a prediction regarding the test molecule and the property modeled by meta-model 310.

While the foregoing is directed to embodiments of the present invention, other and further embodiments of the invention may be devised without departing from the basic scope thereof.

What is claimed is:

1. A method for determining whether one or more test molecules has a biological effect selected from the group consisting of an antibacterial effect, an antiviral effect and an anticancer effect, comprising:

training on a suitably programmed computer more than three different molecular property models using at least one of a first set of training data, wherein each trained molecular property model is configured to generate a molecular property model prediction regarding a property of interest of the one or more test molecules, wherein said molecular property models are used in determining different properties of interest distinct from the biological effect;

using machine learning techniques to train on a suitably programmed computer system a meta-model to predict the biological effect using a second set of training data, wherein a representation of at least one molecule in the second set of training data includes predictions for the one or more test molecules generated by said molecular property models; and establishing a prediction, using the computer implemented trained meta-model, that one or more test molecules has the biological effect based on the molecular property model predictions.

2. The method of claim 1, after the more than three molecular property models are trained, comprising:

selecting the test molecule;

generating a representation of the test molecule for use by the plurality of molecular property models;

providing the representation of the test molecule to the plurality of molecular property models to obtain the molecular property model predictions.

3. The method of claim 2, after the meta-model is trained, comprising:

providing the molecular property model predictions obtained from each of the molecular property models to the meta-model; and generating a biological effect prediction for the test molecule.

4. The method of claim 1, wherein the first set of training data comprises a set of individual training examples, and wherein each example represents at least one molecule, and wherein each training example comprises a representation of the at least one molecule and a value for the property of interest modeled by at least one respective molecular property model.

5. The method of claim 4, wherein training the more than three molecular property models, comprises:

generating a form of each training example for use by a machine learning algorithm; and performing the machine learning algorithm using the set of individual training examples to generate a trained one of the plurality of molecular property models.

6. A method for determining whether one or more test molecules has a biological effect selected from the group consisting of an antibacterial effect, an antiviral effect and an anticancer effect, comprising:

training on a suitably programmed computer more than three different single target activity models using at least one of a first set of training data, wherein each trained single target activity model is configured to generate a molecular property model prediction regarding a property of interest of the one or more test molecules, wherein said single target activity models are used in determining different properties of interest distinct from the biological effect;

using machine learning techniques to train on a suitably programmed computer the meta-model to predict the biological effect using a second set of training data, wherein a representation of at least one molecule in the second set of training data includes predictions for the one or more test molecules generated by said single target activity models; and establishing a prediction, using the computer implemented trained meta-model, that one or more of the test molecules has the biological effect based on the molecular property model predictions.

7. The method of claim 6, after the plurality of single target activity models are trained, comprising:

selecting the test molecule;

generating a representation of the test molecule for use by the more than three single target activity models;

providing the representation of the test molecule to the plurality of single target activity models to obtain the single target activity model predictions.

8. The method of claim 7, after the meta-model is trained, comprising:

providing the single target activity model predictions obtained from each of the single target activity models to the meta-model; and generating a biological effect prediction for the test molecule.

9. The method of claim 6, wherein the first set of training data comprises a set of individual training examples, and wherein each example represents at least one molecule, and wherein each training example comprises a representation of the at least one molecule and a value for the property of interest modeled by each respective single target activity model.

10. The method of claim 9, wherein training a plurality of single target activity models, comprises:

generating a form of each training example for use by a machine learning algorithm; and performing the machine learning algorithm using the set of individual training examples to generate a trained one of the more than three single target activity models.

11. The method of claim 1, wherein one or more of said molecular property models is a single target activity model.

12. The method of claim 11, wherein the single target activity model is configured to predict activity against a non-human target and the meta-model is trained to predict a human biological effect.

13. The method of claim 11, wherein the single target activity model is configured to predict activity against a human target and the meta-model is trained to predict a non-human biological effect.

14. The method of claim 1, wherein one or more of said molecular property models is known not to be associated with the biological effect.

15. The method of claim 1, further comprising:

performing a laboratory experiment for the biological effect on the one or more test molecules predicted to have the biological effect.

16. The method of claim 6, further comprising:

performing a laboratory experiment for the biological effect on the one or more test molecules predicted to have the biological effect.

* * * * *